US012637429B2

(12) United States Patent
Chang et al.

(10) Patent No.: US 12,637,429 B2
(45) Date of Patent: May 26, 2026

(54) OXIDIZED LAPPACONITINE DERIVATIVE AND USE THEREOF

(71) Applicant: QGENETICS CO., LTD., Seoul (KR)

(72) Inventors: Mun Seog Chang, Seoul (KR); Tae Hee Lee, Daejeon (KR); Ha Young Kim, Seoul (KR); Jung Bin Min, Seoul (KR)

(73) Assignee: QGENETICS CO., LTD., Seoul (KR)

( * ) Notice: Subject to any disclaimer, the term of this patent is extended or adjusted under 35 U.S.C. 154(b) by 744 days.

(21) Appl. No.: 17/905,798

(22) PCT Filed: Mar. 5, 2021

(86) PCT No.: PCT/KR2021/002751

§ 371 (c)(1),
(2) Date: Sep. 7, 2022

(87) PCT Pub. No.: WO2021/182803

PCT Pub. Date: Sep. 16, 2021

(65) Prior Publication Data

US 2024/0083851 A1 Mar. 14, 2024

(30) Foreign Application Priority Data

Mar. 9, 2020 (KR) ........................ 10-2020-0028974

(51) Int. Cl.

| | |
|---|---|
| ***C07D 471/22*** | (2006.01) |
| ***A23L 33/10*** | (2016.01) |
| ***A23L 33/105*** | (2016.01) |
| ***A61K 31/439*** | (2006.01) |
| ***A61K 31/55*** | (2006.01) |
| ***A61P 19/00*** | (2006.01) |
| ***A61P 19/10*** | (2006.01) |
| ***C07D 223/32*** | (2006.01) |

(52) U.S. Cl.
CPC ............ *C07D 223/32* (2013.01); *A61K 31/55* (2013.01); *A61P 19/10* (2018.01)

(58) Field of Classification Search
CPC ..... C07D 471/22; A61K 31/439; A61P 19/00; A61P 19/10; A23V 2002/00; A23V 2200/306; A23L 33/10; A23L 33/105
See application file for complete search history.

(56) References Cited

U.S. PATENT DOCUMENTS

2018/0093966 A1 4/2018 Liang et al.
2021/0015881 A1 1/2021 Samorodov

FOREIGN PATENT DOCUMENTS

CN 1305811 A 8/2001
CN 104586879 A 5/2015
CN 107540680 A 1/2018
CN 101480392 A 5/2024
WO WO-2017209653 A1 12/2017

OTHER PUBLICATIONS

Berge, S.M., et al., "Pharmaceutical salts," J. Pharm. Sci. 66(1):1-19, Elsevier, Netherlands (1977).
Bharadwaj, S., et al., "Milk ribonuclease-enriched lactoferrin induces positive effects on bone turnover markers in postmenopausal women," Osteoporos. Int. 20(9):1603-1611, SpringerLink, Germany (2009).
Bruderer, M., et al., "Role and regulation of RUNX2 in osteogenesis," Eur Cell Mater. 28:269-286, AO Research Institute, Switzerland (2014).
Garg, P., et al., "Prospective Review of Mesenchymal Stem Cells Differentiation into Osteoblasts," Orthop. Surg. 9(1):13-19, Tianjin Hospital and John Wiley & Sons Australia, Ltd., Australia (2017).
Greenblatt, M.B., et al., "Mitogen-activated protein kinase pathways in osteoblasts," Annu. Rev. Cell Dev. Biol. 29:63-79, Annual Reviews, United States (2013).
International Search Report for International Application No. PCT/KR2021/002751, Korean Intellectual Property Office, Daejeon, South Korea, mailed on Jun. 22, 2021, 7 pages.
Lee, N.K., et al., "Endocrine regulation of energy metabolism by the skeleton," Cell 130(3):456-469, Cell Press, United States (2007).
Sun, J., et al., "Role of bone morphogenetic protein-2 in osteogenic differentiation of mesenchymal stem cells," Mol. Med. Rep. 12(3):4320-4237, Spandidos Publications, Greece (2015).
Tsyrlina, E.M., et al., "Isoxazolidine derivatives of lappaconitine and talatisamine," Chemistry of Natural Compounds 54(3):515-519, Springer Science+Business Media, Germany (2018).
Turabekova, M.A., et al., "Aconitum and Delphinium alkaloids "Drug-likeness" descriptors related to toxic mode of action," Environ. Toxicol. Pharmacol. 25(3):310-320, Elsevier, Netherlands (2008).
Wang, J.L., et al., "Structure-analgesic activity relationship studies on the C(18)- and C(19)- diterpenoid alkaloids," Chem. Pharm. Bull. (Tokyo). 57(8):201-208, Pharmaceutical Society of Japan, Japan (2009).
Xu, H., et al., "Pain-relieving effects of processed Aconiti tuber in CCI-neuropathic rats," J. Ethnopharmacol. 275:114126, Elsevier, Netherlands (2006).
Deng, X., et al., "The inhibitory effect of Aconiti Sinomontani Radix extracts on the proliferation and migration of human synovial fibroblast cell line SW982," J Ethnopharmacol 213:321-327, Elsevier, Netherlands (Mar. 2018).
Traditional Knowledge Digital Library—Traditional Knowledge Resource, "BP/1007 J¢ t¤phal¢ dyava°ik¢," pp. 1-5 (Dec. 1990).

*Primary Examiner* — Brenda L Coleman
(74) *Attorney, Agent, or Firm* — Myers Bigel, P.A.

(57) ABSTRACT

The present invention relates to a novel lappaconitine derivative and a pharmaceutically acceptable salt thereof, a preparation method therefor, and a medical use thereof using osteogenesis-promoting activity. The lappaconitine derivative induces the differentiation of stem cells into preosteoblasts, and increases bone density when administered to an osteoporosis animal model, and induces osteogenesis, and thus can be effectively used for preventing, alleviating, or treating bone-related diseases such as osteoporosis.

9 Claims, 17 Drawing Sheets

A

B

| Inhibitors (targets) | LAD activity |
|---|---|
| PD (PD0325901) (ERK) | Inhibition |
| SP (SP600125) (JNK) | Inhibition |
| SB (SB203580) (p38 MAPK) | Inhibition |
| 53AH (Wnt) | Partial inhibition |
| WP (WP1066) (STAT3) | Partial inhibition |
| LY (LY294002) (PI3K/AKT) | Partial inhibition |

| Animal group | Concentration | Administration |
|---|---|---|
| Sham+$H_2O$ | 0.3ml/kg/day | Oral |
| OVX+$H_2O$ | 0.3ml/kg/day | Oral |
| OVX+Fosamax | 0.5 mg/kg/day | Subcutaneous |
| OVX+Forteo | 0.02 mg/kg/day | Subcutaneous |
| OVX+LAD | 5 mg/kg/day | Oral |
| | 30 mg/kg/day | |

OXIDIZED LAPPACONITINE DERIVATIVE AND USE THEREOF

TECHNICAL FIELD

The present invention relates to a novel oxidized lappaconitine derivative and a pharmaceutically acceptable salt thereof, which belong to the diterpenoid alkaloid family, a method of preparing the same, and a medical use thereof using osteogenesis-promoting activity.

BACKGROUND ART

Aconitine, which is one of components of *Aconiti lateralis* Radix as an herbal medicine, is the most toxic chemical compound that belongs to the alkaloid family. However, when *Aconiti lateralis* Radix is boiled into a decoction, it has reduced toxicity. Similarly, when heat is directly applied to such a compound, it is converted into less toxic compounds such as benzoylaconine, aconine, and the like through deacetylation or debenzoylation. Based on this principle, *Aconiti lateralis* Radix (processed *Aconiti lateralis* Radix or purified *Aconiti lateralis* Radix) whose toxicity is reduced through the heat treatment has been used as an herbal drug to reduce inflammation and pain in patients with neuralgia (Xu et al., *J Ethnopharmacol* 2006).

Separately, hundreds of various alkaloid compounds, such as deoxyaconitine, mesaconitine, hypaconitine, lappaconitine, and the like, which have a similar chemical structure, and belong to the diterpenoid alkaloid family such as aconitine, have been studied through semisynthesis and structural confirmation, and their biological activity has also been elucidated (Turabekova et al., *Environ Toxicol Pharmacol.* 2008). For example, Shaanxi University of Science & Technology has released the results showing that lappaconitine exhibits anticancer activity by removing a 2-acetaminobenzoyl group at the carbon 4 position of lappaconitine and attaching various cinnamic derivatives thereto. The same university has also synthesized various compounds by varying the group at position 4 and functional groups at positions 8 and 9 (Liangcheng et al., CN 107540680 A, published on Jan. 5, 2018). Dr Vladimirovich (Russia) has also confirmed the inflammatory action of lappaconitine derivatives to which various aromatic compounds are attached at position 4 of lappaconitine (S. V. Vladimirovich, WO 2017/209653 A1).

Among many alkaloid compounds, lappaconitine is known to exhibit various effects such as antiarrhythmic, anti-inflammatory, antioxidant, anticancer and antiepileptic effects (Wang et al., Chem Pharm Bull. 2009). The present inventors have prepared novel derivatives by oxidizing lappaconitine while conducting research on new pharmacological activities of lappaconitine, and found that the novel derivatives promote osteogenesis. Therefore, the present invention has been completed based on these facts.

DISCLOSURE

Technical Problem

According to one aspect of the present invention, the present invention is directed to providing a novel oxidized lappaconitine derivative having an osteogenesis-promoting function and an ability to treat osteoporosis, a method of preparing the same, and a pharmaceutical composition for preventing, ameliorating or treating a bone-related disease, which includes the oxidized lappaconitine derivative as an active ingredient.

Technical Solution

To achieve the objects of the present invention as described above, according to one aspect of the present invention, there is provided a compound represented by the following Formula 1, and a stereoisomer, a hydrate, a solvate, or a pharmaceutically acceptable salt thereof.

[Formula 1]

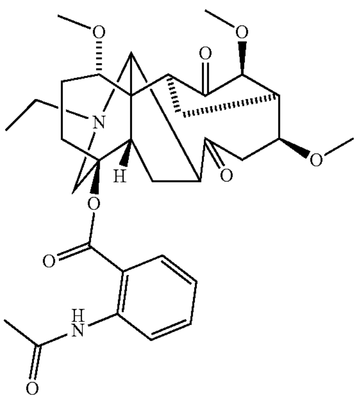

According to one embodiment of the present invention, the compound of Formula 1 is (3S,6S,7S,9S,11S,16S)-1-ethyl-6,9,11-trimethoxy-8,13-dioxododecahydro-2H-3,6a,14-(epiethane[1,1,2]triyl)-7,10-methanocyclodeca[b]azocin-3(4H)-yl 2-acetaminobenzoate.

In the present invention, the compound of Formula 1 includes a hydrate, a solvate, stereoisomer, and a radioactive derivative thereof, as well as the compound represented by Formula 1 and a pharmaceutically acceptable salt thereof.

The term "pharmaceutically acceptable salt" refers to a salt that is suitable for use in contact with the tissue from humans and lower animals without causing excessive toxicity, stimulations, allergic reactions, and the like within the scope of sound medical judgment and does not have an adverse effect on the biological activity and physicochemical properties of a parental compound. The pharmaceutically acceptable salt is well known in the art. For example, the pharmaceutically acceptable salts are described in detail in S. M. Berge et al., J. Pharmaceutical Sciences, 66, 1, 1977. The salt may be prepared in situ while finally separating and purifying the compound of the present invention, or separately prepared through a reaction with an inorganic base or an organic base. For example, suitable addition salt forms include ammonium salts; alkali metal salts such as salts of lithium, sodium, potassium, magnesium, calcium, and the like, and alkaline earth metal salts (calcium salt, and the like); salts with organic bases, for example, primary, secondary, and tertiary aliphatic and aromatic amines (such as methylamine, ethylamine, propylamine, isopropylamine), quaternary butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, benzathine, N-methyl-D-glucamine, 2-amino-2-(hydroxymethyl)-1,3-propanediol, hydrabamine salt; and salts with amino acids such as arginine, lysine, and the like.

In the present invention, the hydrate or solvate of the compound of Formula 1 may be prepared using a conventional method, for example prepared by dissolving the base compound of Formula 1 in a solvent such as water, methanol, ethanol, acetone, 1,4-dioxane, adding a free acid or a free base thereto, and crystallizing or recrystallizing the resulting mixture.

Also, the compound of Formula 1 may have one or more asymmetric centers. In this case, an enantiomer or a diastereoisomer may be present for such a compound. Therefore, the compound of the present invention includes either an enantiomer or a diastereoisomer or an isomer mixture thereof. Also, the different isomers may be separated or decomposed using a conventional method, or any isomers may be obtained by a conventional synthesis method or through stereospecific or asymmetric synthesis. In addition, the compound of the present invention includes radioactive derivatives of the compound represented by Formula 1, and these radioactive compounds are useful in the field of biological research.

In the present invention, the compound of Formula 1 may be prepared by allowing lappaconitine to react with an oxidizing agent.

According to one embodiment of the present invention, the lappaconitine may be lappaconitine hydrogen bromide. In this case, a process of removing hydrogen bromide may be further included before allowing the lappaconitine to react with the oxidizing agent. For example, a process of removing hydrogen bromide from the lappaconitine hydrogen bromide may be performed using dichloromethane ($CH_2Cl_2$) in the presence of a base as shown in the following Scheme 1.

[Scheme 1]

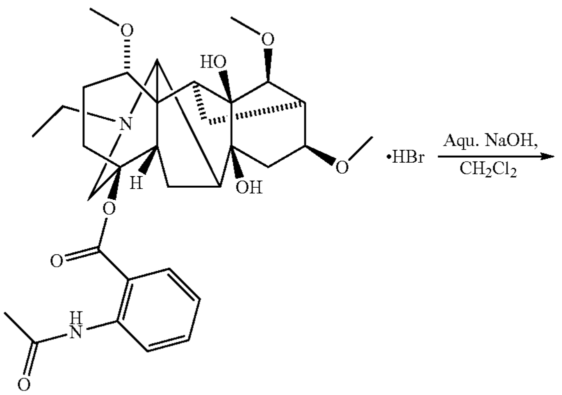

<Lappaconitine/HBr>

-continued

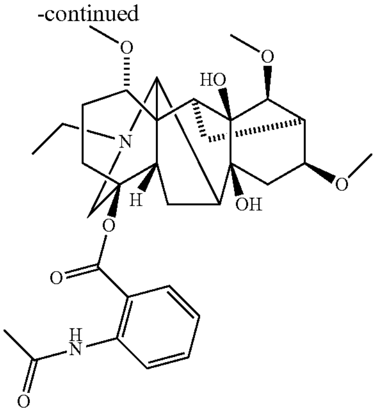

<Lappaconitine>

Next, the lappaconitine may be oxidized through reaction with an oxidizing agent, as shown in the following Scheme 2, thereby generating a lappaconitine derivative (LAD), which is the compound of Formula 1. The oxidizing agent may be selected from the group consisting of phenyliodine diacetate ($PhI(OAc)_2$, lead (II) acetate ($Pb(CH_3CO_2)_2$), lead (II) acetate ($Pb(CH_3CO_2)_4$), ozone, and $HIO_4$, each of which is dissolved in dimethylformamide (DMF).

[Scheme 2]

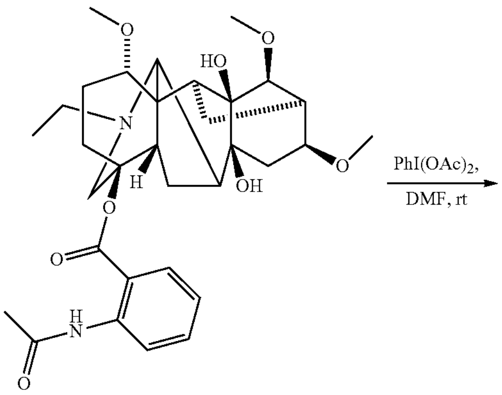

<Lappaconitine>

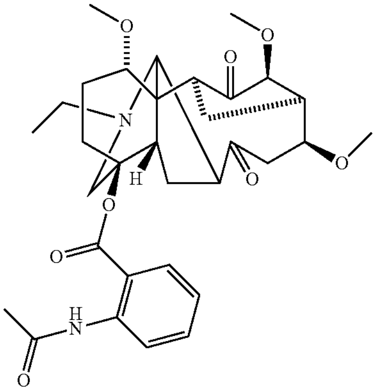

<LAD>

In the present invention, the compound of Formula 1 synthesized by the method may be separated using typical separation and purification processes, for example, by diluting the mixture in an organic solvent, washing the mixture, and concentrating an organic layer under reduced pressure. When necessary, the compound of Formula 1 may be purified by column chromatography and a recrystallization method using various solvents.

The present inventors have synthesized the novel compound of Formula 1 by hydrolyzing lappaconitine, which has the anti-inflammatory, antioxidant, anticancer effects, and the like, while conducting research on the new pharmacological activity of lappaconitine, and found that such a compound promotes osteogenesis.

Therefore, another aspect of the present invention provides a pharmaceutical composition for preventing or treating a bone-related disease, which includes the compound represented by Formula 1 or a pharmaceutically acceptable salt thereof as an active ingredient.

In the pharmaceutical composition, the compound represented by Formula 1 or pharmaceutically acceptable salt thereof includes a hydrate, a solvate, a stereoisomer, and a radioactive derivative thereof.

According to one embodiment of the present invention, the compound of Formula 1 may promote the differentiation of stem cells into osteoblasts, and increase the expression of an osteogenic marker selected from the group consisting of runt-related transcription factor 2 (RUNX2), bone morphogenetic protein 2 (BMP2), and osteocalcin, and thus may aid osteogenesis. Mesenchymal stem cells, hematopoietic stem cells, adipose stem cells, bone marrow stem cells, and the like may be used as the stem cells.

In the present invention, the bone-related disease may be selected from the group consisting of osteoporosis, bone fractures, rheumatoid arthritis, periodontitis, osteomalacia, osteopenia, bone atrophy, osteoarthritis, bone defects, osteolysis, and osteonecrosis. Preferably, the bone-related disease may be osteoporosis.

The term "osteoporosis" as used in this specification refers to a condition in which a microstructure of the bone tissue degenerates due to a decrease in minerals (particularly calcium) and matrices, which constitute bone, resulting in a consistent rise in the risk of bone fracture. Types of osteoporosis includes primary osteoporosis such as postmenopausal osteoporosis and senile osteoporosis, and secondary osteoporosis caused by diseases, drugs, drinking, smoking, and the like, all of which affect the formation and loss of bone.

The pharmaceutical composition of the present invention may further include a carrier, an excipient, and a diluent suitable for common use in the preparation of medicines in addition to the compound of Formula 1 included as the active ingredient. The carrier, the excipient, and the diluent that may be included in the pharmaceutical composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxy benzoate, talc, magnesium stearate, mineral oil, and the like.

When the pharmaceutical composition of the present invention is formulated, the pharmaceutical composition is prepared using a commonly used diluent or excipient such as a filler, an extender, a binder, a wetting agent, a disintegrant, a surfactant, and the like. A solid preparation for oral administration includes a tablet, a pill, a powder, a granule, a capsule, and the like. Such a solid preparation is prepared by mixing the composition of the present invention with one or more excipients, for example, starch, calcium carbonate, sucrose or lactose, gelatin, and the like. Also, lubricants such as magnesium stearate, talc, and the like are used in addition to the simple excipients. A liquid preparation for oral administration is a suspension, a solution, an emulsion, a syrup, or the like, and thus may include various excipients, for example, a wetting agent, a sweetening agent, a flavoring agent, a preservative, and the like in addition to commonly used simple diluents (such as water, liquid paraffin, and the like). A preparation for parenteral administration includes a sterile aqueous solution, a non-aqueous solvent, a suspension, an emulsion, a lyophilized preparation, a suppository, and the like. Propylene glycol, polyethylene glycol, a vegetable oil such as olive oil, and the like, injectable esters such as ethyl oleate, and the like may be used as the non-aqueous solvent and the suspension.

The pharmaceutical composition of the present invention may be orally or parenterally administered, and a preferred dose of the composition of the present invention may depend on the condition and weight of a patient, the severity of a disease, the type of drug, a route of administration, and the administration duration, but may be suitably selected by those skilled in the art. For example, the dose of the compound of Formula 1 may depend on the age, weight, and gender of a patient, an administration mode, the health condition, and the severity of a disease. To an adult patient weighing 70 kg, the compound of Formula 1 may be generally administered daily at a dose of 0.01 mg to 5,000 mg. The dose may be administered once a day or in divided doses. In this case, the dose is intended to limit the scope of the present invention in any way.

Also, the present invention provides a method of treating a bone-related disease, which includes administering the pharmaceutical composition to a subject in need of treatment. The type of bone-related disease and the dose of the pharmaceutical composition are as described above in the pharmaceutical composition for preventing or treating a bone-related disease.

In the present invention, when the pharmaceutical composition for preventing or treating a bone-related disease is orally administered, the pharmaceutical composition for oral administration may be a solid preparation, a semisolid preparation, or a liquid preparation for oral administration. The solid preparation for oral administration may be, for example, a tablet, a pill, a hard or soft capsule, a powder, a fine granule, a granule, a powder for reconstituting a solution or a suspension, a lozenge, a wafer, an oral film (an oral strip) a dragee, a chewable gum, and the like, but the present invention is not limited thereto. The liquid preparation for oral administration includes a solution, a suspension, an emulsion, a syrup, an elixir, a spirit, aromatic water, a lemonade, an extract, a precipitate, a tincture, and an infused oil.

In the present invention, when the pharmaceutical composition for preventing or treating a bone-related disease is used as an injection, the pharmaceutical composition may be directly administered to the site of bone-related disease. When the pharmaceutical composition is formulated into an injection, the injection may include a non-toxic buffered solution, which is isotonic with blood, as the diluent, for example, a phosphate buffered solution having a pH of 7.4. The injection may include other diluents or additives in addition to the buffered solution.

Also, in the present invention, the pharmaceutical composition may be implanted into a treatment site after it is mixed with an excipient such as a collagen sponge.

Another aspect of the present invention provides a food composition for preventing or ameliorating a bone-related disease, which includes the compound represented by Formula 1 or a pharmaceutically acceptable salt thereof as an active ingredient.

In the food composition, the compound represented by Formula 1 or a pharmaceutically acceptable salt thereof includes a hydrate, a solvate, and a stereoisomer thereof.

The same components as in the pharmaceutical composition for preventing or treating a bone-related disease are used in the food composition, and thus the overlapping content between the pharmaceutical composition and the food composition is omitted to avoid the unnecessary description of this specification.

In the present invention, the food composition may be provided in the form of a powder, a granule, a tablet, a capsule, a syrup, a drink, or a pill. In this case, the food composition may be used together with other foods or food additives in addition to the compound represented by Formula 1 as the active ingredient, and may be suitably used according to the conventional methods. A mixing amount of the active ingredient may be suitably determined depending on the purpose of use, for example, prevention, health, or therapeutic treatment.

An effective dose of the active ingredient included in the food composition may be used based on the effective dose of the pharmaceutical composition. However, when the active ingredient is taken for a long period for the purpose of health and hygiene or for the purpose of regulating health, the food composition is administered at a dose less than the effective dose range. It is certain that the active ingredient may be used at a dose greater than the effective dose range because the active ingredient has no problems in terms of safety.

The food composition includes components commonly added during the preparation of food. For example, the food composition includes proteins, carbohydrates, fats, nutrients, seasonings, and flavoring agents. Examples of the above-described carbohydrates include monosaccharides, for example glucose, fructose, and the like; disaccharides, for example maltose, sucrose, oligosaccharides, and the like; and polysaccharides, for example conventional sugars, such as dextrin, cyclodextrin, and the like; and sugar alcohols such as xylitol, sorbitol, erythritol, and the like. A natural flavoring agent and a synthetic flavoring agent may be used as the flavoring agent. For example, when the food composition of the present invention is prepared as drinks, the food composition may further include citric acid, liquid fructose, sugar, glucose, acetic acid, malic acid, fruit juice, and the like in addition to the active ingredient of the present invention.

Still another aspect of the present invention provides a composition for inducing the in vitro differentiation into osteoblasts using the compound represented by Formula 1.

According to one embodiment of the present invention, when mesenchymal stem cells are treated with the compound represented by Formula 1, calcium and mineral production may be increased, thereby promoting the differentiation of stem cells into osteoblasts.

Advantageous Effects

An oxidized lappaconitine derivative of the present invention induces the differentiation of stem cells into osteoblasts, increases bone mineral density when administered to an animal model of osteoporosis, and induces osteogenesis, and thus can be effectively used for preventing, ameliorating, or treating bone-related diseases such as osteoporosis.

BEST MODE

Figure 1A:
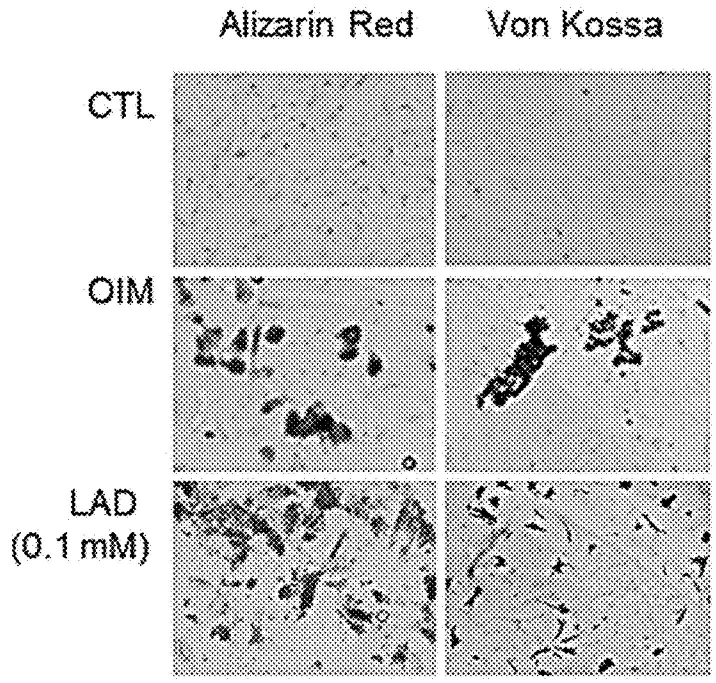
FIG. 1A shows the results of confirming levels of calcium (Alizarin Red) and mineral production (Von Kossa) after mesenchymal stem cells are treated with a lappaconitine derivative (LAD).

Hereinafter, one or more embodiments of the present invention will be described in detail with reference to examples thereof. However, it should be understood that the examples are for exemplary illustration and are not intended to limit the scope of the present invention.

Preparation Example: Preparation of LAD

1-1. Preparation of Lappaconitine

Dichloromethane (500 mL) and an aqueous sodium hydroxide solution (10 g of NaOH, and 100 g of water) were added to lappaconitine.hydrogen bromide (10.08 g, 0.017 mol), and an organic layer and an aqueous layer were separated using a separatory funnel. The separated organic layer was washed several times with water, dried over anhydrous magnesium sulfate, and then distilled to obtain the target lappaconitine with a yield of 89% (8.90 g).

$^1$H-NMR ($CDCl_3$, 400 MHz) δ 10.98 (s, 1H), 8.60 (d, J=8.4 Hz, 1H), 7.86-7.83 (m, 1H), 7.42 (t, 1H), 6.95 (t, 1H), 3.52-3.37 (m, 2H), 3.36-3.35 (m, 2H), 3.36 (s, J=7.1 Hz, 3H), 3.22 (s, 3H), 3.13 (s, 3H), 3.11-3.09 (m, 2H), 2.60-2.46 (m, 10H), 2.15 (s, 3H), 2.14-1.73 (m, 6H), 1.74-1.68 (m, 1H), 1.74-1.70 (m, 1H), 1.06 (t, J=6.8 Hz, 3H);

$^{13}$C-NMR ($CDCl_3$, 100 MHz) δ 169.02, 167.39, 141.6, 134.34, 131.07, 122.31, 120.19, 115.76, 90.10, 84.62, 84.13, 82.89, 78.57, 75.56, 61.48, 57.89, 56.52, 56.10, 55.50, 50.85, 49.86, 48.97, 48.51, 47.61, 44.76, 36.28, 31.83, 26.77, 26.20, 25.53, 24.12, 13.53;

HRMS ($ES^+$): m/z calculated for $C_{32}H_{44}N_2O_8$: 585.3098 $[M+H]^+$.

Found 585.3176.

1-2. Preparation of Lappaconitine Derivative (LAD) from Lappaconitine

Lappaconitine (8.9 g, 0.015 mol) was slowly added to a solution in which phenyliodine diacetate ($PhI(OAc)_2$ (14.07 g, 0.044 mol) was dissolved in dimethylformamide (DMF, 150 mL), and stirred for 10 minutes. When the reaction was completed, the solution was diluted with ethyl acetate (EA), and extracted using an aqueous solution of saturated sodium bicarbonate ($NaHCO_3$). The organic layer was washed several times with water to remove dimethylformamide, dried over anhydrous magnesium sulfate, and then distilled under reduced pressure. The resulting crude product was separated by column chromatography (diethyl ether:ethyl acetate: hexane=3:2:5) to obtain {(3S,6S,7S,9S,11S,16S)-1-ethyl-6,9,11-trimethoxy-8,13-dioxododecahydro-2H-3,6a,14-(epi-ethane[1,1,2]triyl)-7,10-methanocyclodeca[b]azocin-3(4H)-yl 2-acetaminobenzoate} as the target lappaconitine derivative (LAD) with a yield of 25.7% (2.3 g).

$^1$H-NMR ($CDCl_3$, 400 MHz) δ 10.99 (s, 1H), 8.62 (d, J=8.4 Hz, 1H), 7.89 (d, J=9.6 Hz, 1H), 7.47-7.43 (m, 1H), 7.01-6.99 (m, 1H), 3.88-3.64 (m, 4H), 3.65 (s, 3H), 3.41 (s, 3H), 3.18 (s, 3H), 2.90-2.25 (5, 4H), 2.20 (s, 3H), 2.19-1.80 (m, 4H), 1.15 (t, J=7.0 Hz, 3H);

$^{13}$C-NMR ($CDCl_3$, 100 MHz) δ 211.85, 204.31, 169.10, 167.40, 162.18, 143.74, 141.74, 134.61, 131.07, 122.41, 120.30, 115.45, 86.92, 82.75, 81.45, 78.21, 76.28, 60.73, 58.17, 57.37, 54.35, 52.98, 50.19, 48.78, 46.06, 45.92, 38.41, 32.06, 25.56, 25.39, 25.36, 12.72;

HRMS ($ES^+$): m/z calculated for $C_{32}H_{42}N_2O_8$: 583.3018 $[M+H]^+$.

Found 583.2941.

Experimental Example 1: (In Vitro) Confirmation of Efficacy of LAD

1-1. Confirmation of Osteocytic Differentiation Potential of LAD in MSCs

Osteoblasts involved in osteogenesis are formed by differentiating mesenchymal stem cells (MSCs) using external stimuli and transcription factors involved in various signaling pathways (Garg et al., Orthop Surg. 2017). Accordingly, an experiment was performed to check whether LAD was able to induce the differentiation of human MSCs into osteoblasts.

MSCs from a normal human were purchased from the American Type Culture Collection (ATCC, U.S.A), and cultured in an MSC-specific culture medium (Gibco). The cultured cells were digested with trypsin, centrifuged, and then seeded in a 24-well plate at a concentration of $3\times10^4$ cells/well. The next day, the MSC culture medium was exchanged with a DMEM medium (DMEM/10% FBS/penicillin/streptomycin) as an experimental medium, and the cells were treated with LAD alone (0.1 μM) or OIM (osteogenesis-inducing medium; StemPro Osteogenesis Differentiation Kit, ThermoFisher Scientific Inc.) as the positive control. Thereafter, the cell culture medium was exchanged with a fresh DMEM medium every day, treated with LAD or OIM, and then cultured for 3 weeks. After the culture was completed, the cells were stained with Alizarin Red for detection of calcium and Von Kossa for detection of mineral production.

Figure 1B:
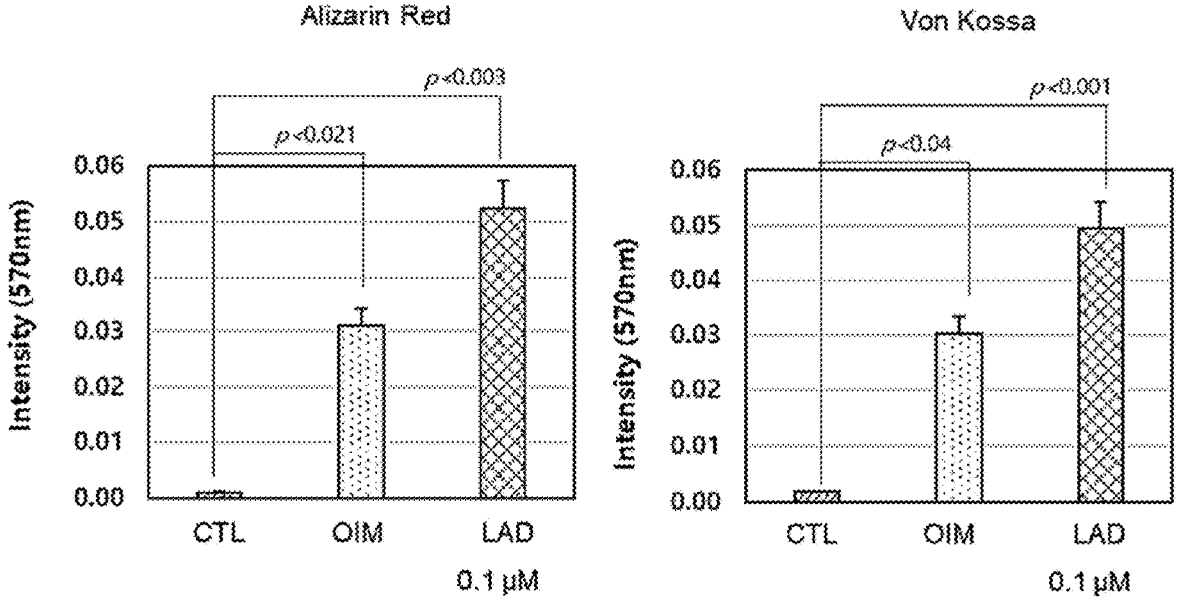
FIG. 1B is a graph showing the staining results of FIG. 1A.

Based on the staining results, it can be seen that LAD induced calcium and mineral production in human MSCs like the OIM as the positive control for osteoblast differentiation (FIGS. 1A and 1B). The results show that the LAD may differentiate MSCs into osteoblasts at the cellular level.

1-2. Confirmation of Change in Expression of RUNX2 and BMP2 in MSCs

Runt-related transcription factor 2 (RUNX2; core-binding factor alpha, Cbfa1) is the most important transcriptional regulatory factor for osteogenesis, and is known to be involved in osteoblast differentiation, matrix generation, and mineralization during the osteogenesis (Bruderer M, et al., Eur Cell Mater. 2014). Also, RUNX2 itself may be regulated by a bone morphogenetic protein (BMP), which is a type of cytokine (Sun J, et al., Mol Med Rep. 2015). Accordingly, it was confirmed whether LAD promotes the expression of an osteogenesis-related specific factor to induce osteogenesis.

MSCs were seeded in a 24-well plate at a concentration of $3\times10^4$ cells/well, and cultured for 24 hours. From the next day, the MSCs were treated with different concentrations (0.001 μM, 0.01 μM, and 0.1 μM) of LAD once a day for 7 days and 14 days. After the experiment was completed, the MSCs were stained with RUNX2 and BMP-2 antibodies, and observed using a fluorescence microscope.

Figure 2A:
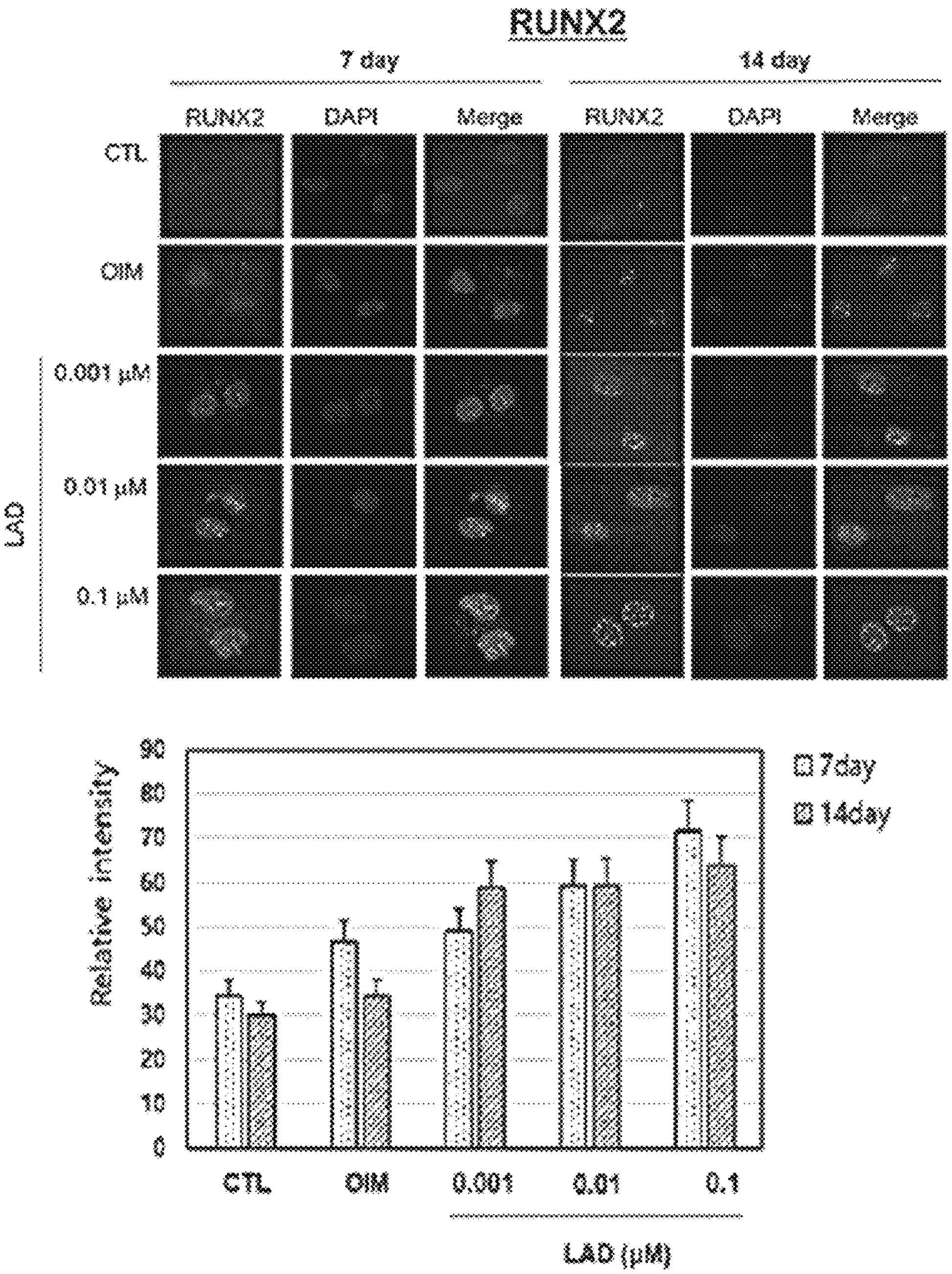
FIG. 2A shows the results of confirming a change in expression of RUNX2 after mesenchymal stem cells are treated with various concentrations of the lappaconitine derivative (LAD) for a predetermined time.
Figure 2B:
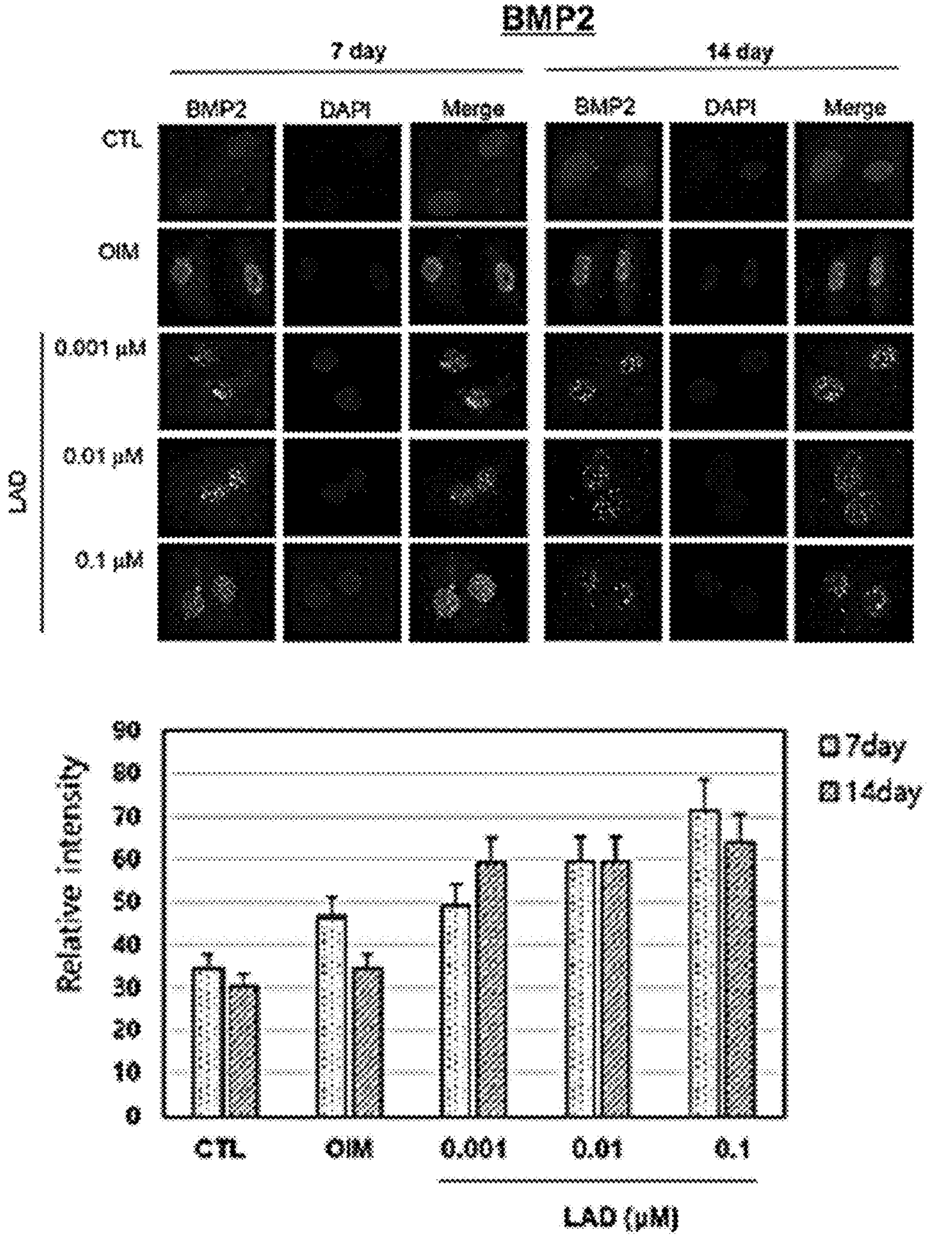
FIG. 2B shows the results of confirming a change in expression of BMP2 after mesenchymal stem cells are treated with various concentrations of the lappaconitine derivative (LAD) for a predetermined time.

As a result, it can be seen that LAD strongly induced the expression of RUNX2 and BMP-2 even at a low concentration (0.001 μM=1 nM), and this tendency increased with an increasing concentration (FIGS. 2A and 2B). The results show that the LAD may be involved in osteogenesis at the molecular level by differentiating human MSCs into osteoblasts.

1-3. Confirmation of Change in Expression of Osteocalcin in MSCs

Osteocalcin is expressed only in osteoblasts (Lee et al., Cell 2007), and is used as a useful biomarker for osteogenesis (Bharadwaj et al., Osteoporosis International, 2009). Accordingly, it was confirmed that LAD had an effect on the expression of osteocalcin which is an osteoblast-specific marker.

Figure 3A:
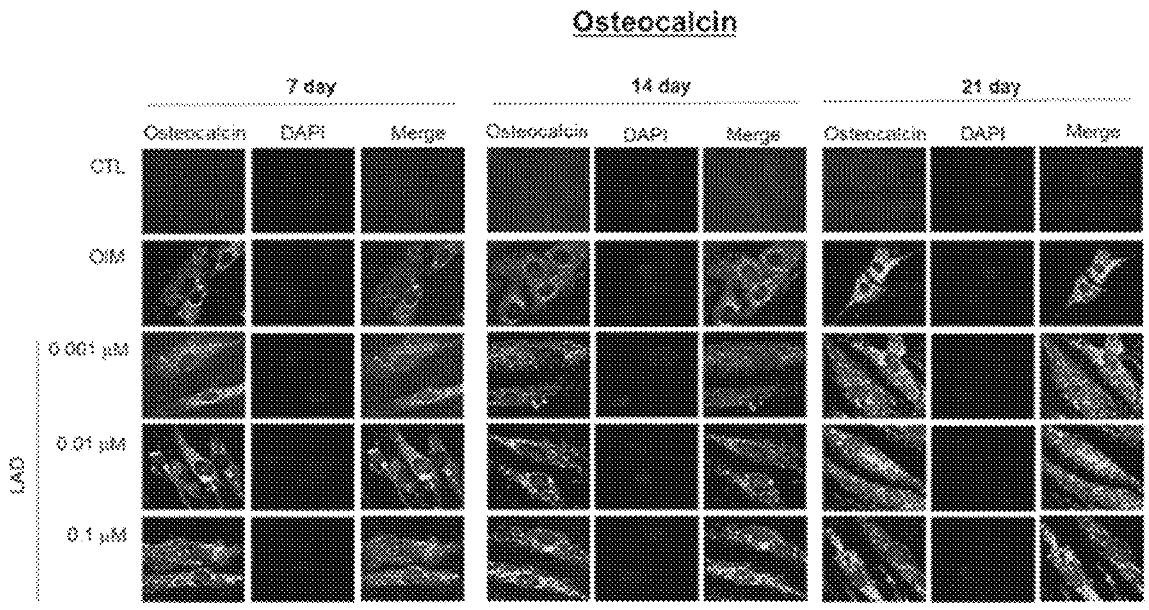
FIG. 3A shows the results of confirming a change in expression of osteocalcin using a fluorescence microscope after mesenchymal stem cells are treated with various concentrations of the lappaconitine derivative (LAD) for a predetermined time.
Figure 3B:
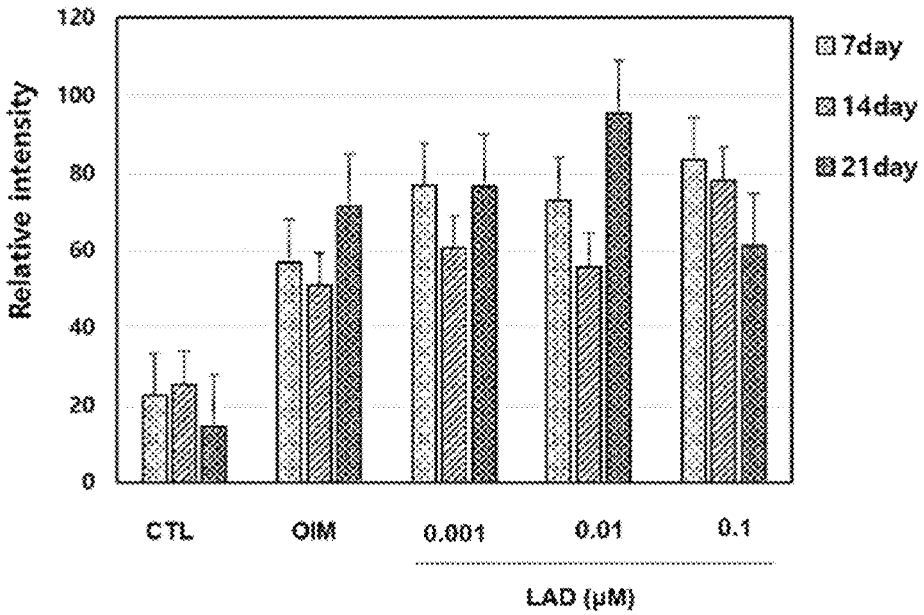
FIG. 3B is a graph showing the fluorescence levels of FIG. 3A.

An experiment was performed in the same manner as described in Experimental Example 1-2, and MSCs were then stained with an osteocalcin antibody, and observed using a fluorescence microscope. As a result, it was confirmed that LAD strongly induced the expression of osteocalcin within 7 days after the cells were treated with a low concentration (0.001 μM) of LAD, indicating that the expression level was similar to that of the OIM-treated group as the positive control (FIGS. 3A and 3B).

1-4. Confirmation of Mechanism of Differentiation of MSCs into Osteoblasts

To study a mechanism by which LAD differentiates MSCs into osteoblasts, related signaling was investigated.

MSCs cultured in an experimental DMEM culture medium were treated with LAD (1 μM) or the control compound (DMSO), and cultured for 24 hours. The cells were recovered, and an experiment was then performed according to a method specified in a phosphokinase antibody array kit (R&D Systems) containing antibodies that specifically recognize phosphorylated forms of 43 kinases. Then, samples were analyzed using an ImageJ (NIH, USA) program.

Figure 4A:
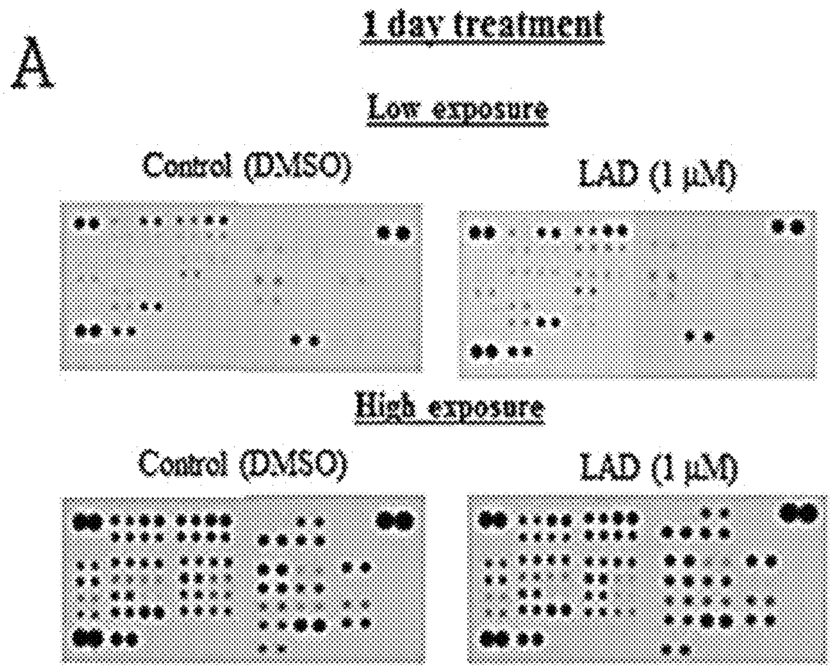
FIG. 4A shows the results of confirming phosphorylation levels of various kinases after mesenchymal stem cells are treated with the lappaconitine derivative (LAD).
Figure 4B:
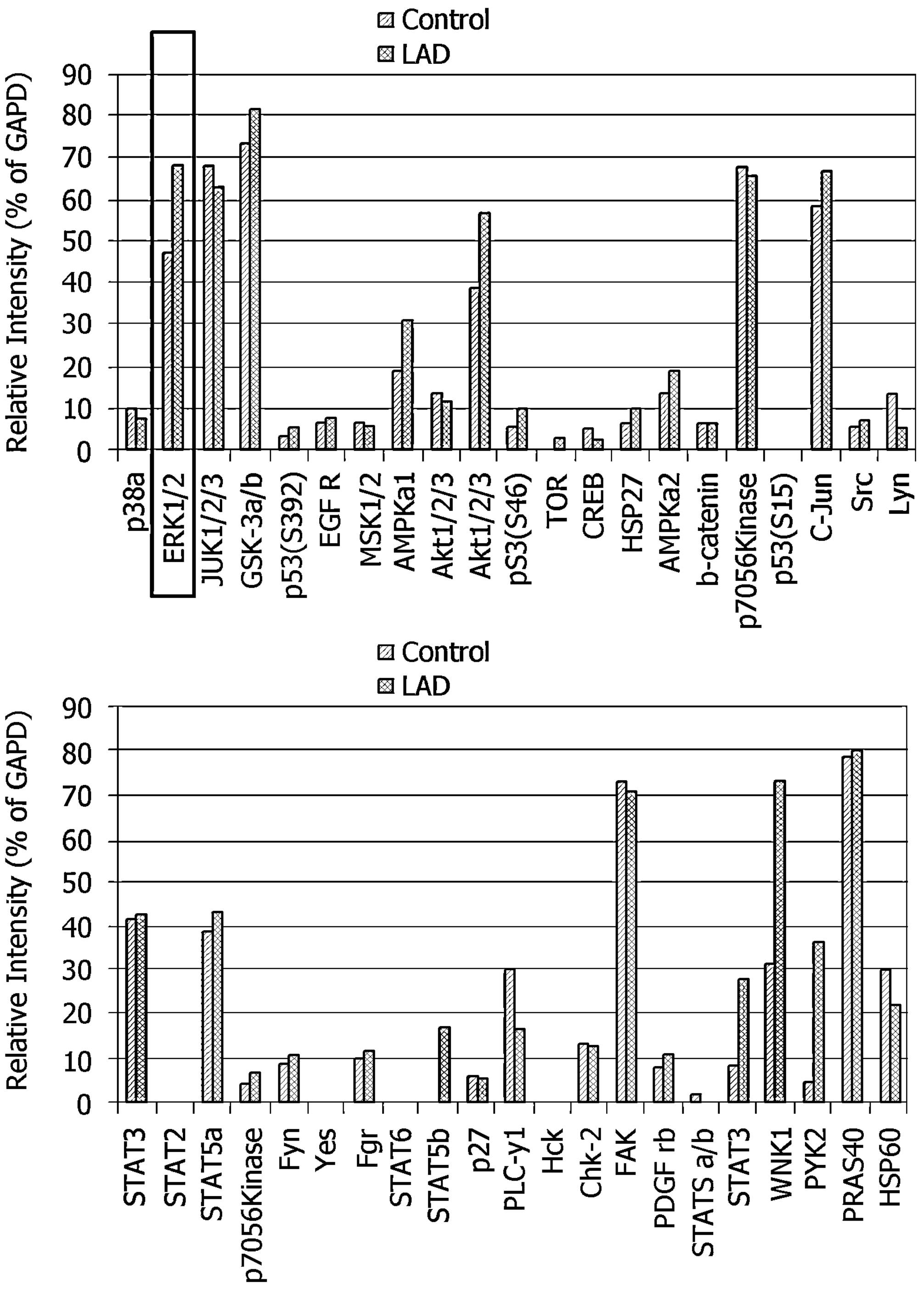
FIG. 4B is a graph showing the phosphorylation levels confirmed in FIG. 4A.

Based on the results of analysis, it can be seen that LAD strongly increased the phosphorylation of signaling molecules such as ERK, Akt, WNK1, and the like compared to the control DMSO (FIGS. 4A and 4B).

1-5. Confirmation of Mechanism of Differentiation of MSCs into Osteoblasts

To further study the mechanism by which LAD differentiates MSCs into osteoblasts, an experiment was performed using a kinase inhibitor.

After MSCs were cultured, the MSCs were simultaneously treated with a kinase inhibitor (1 μM) and LAD (1 μM). Next day, the medium was exchanged, and the MSCs were simultaneously treated again with the kinase inhibitor and LAD. This procedure was repeated for 3 weeks, and the MSCs were than stained with Alizarin Red.

Figure 5:
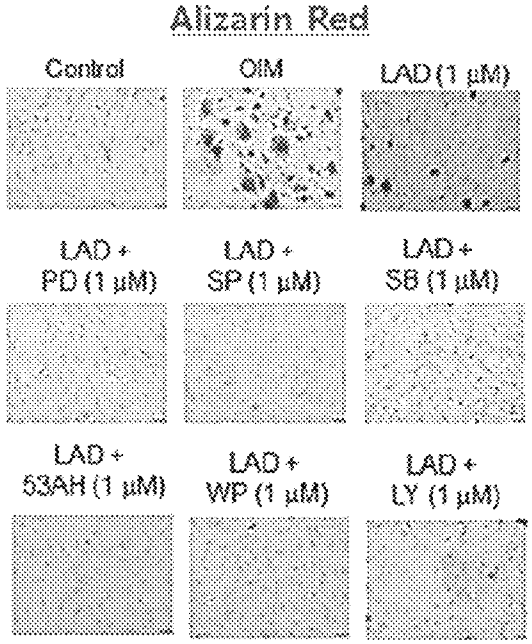
FIG. 5 shows the results of confirming calcium levels after mesenchymal stem cells are treated with a combination of the lappaconitine derivative (LAD) and various kinase inhibitors.

As a result, it can be seen that osteoblast differentiation ability of LAD was inhibited in the experimental group treated with a combination of LAD and the inhibitor, which inhibits ERK, P38, or Akt, compared to the LAD-alone-treated group (FIG. 5). These results show that LAD is involved in the differentiation of MSCs into osteoblasts by activating the signaling of these enzymes.

1-6. Confirmation of Effect on ERK Phosphorylation in MSCs

Previous research shows that an MAP-kinase signaling mechanism including ERK and p38 plays an important role in osteoblast differentiation (Greenblatt et al., MB, Annu Rev Cell Dev Biol. 2013). Similar to the results of previous research, the results of Experimental Example 1-5 show that LAD shows the potential to differentiate MSCs into osteoblasts through ERK and p38 MAP-kinases (FIG. 5). Also, the results of Experimental Example 1-4 show that LAD has the potential to induce osteoblast differentiation through the phosphorylation of ERK rather than p38 (FIG. 4). Accordingly, the level of phosphorylated ERK according to time elapsed after MSCs were treated with LAD was determined.

Figure 6A:
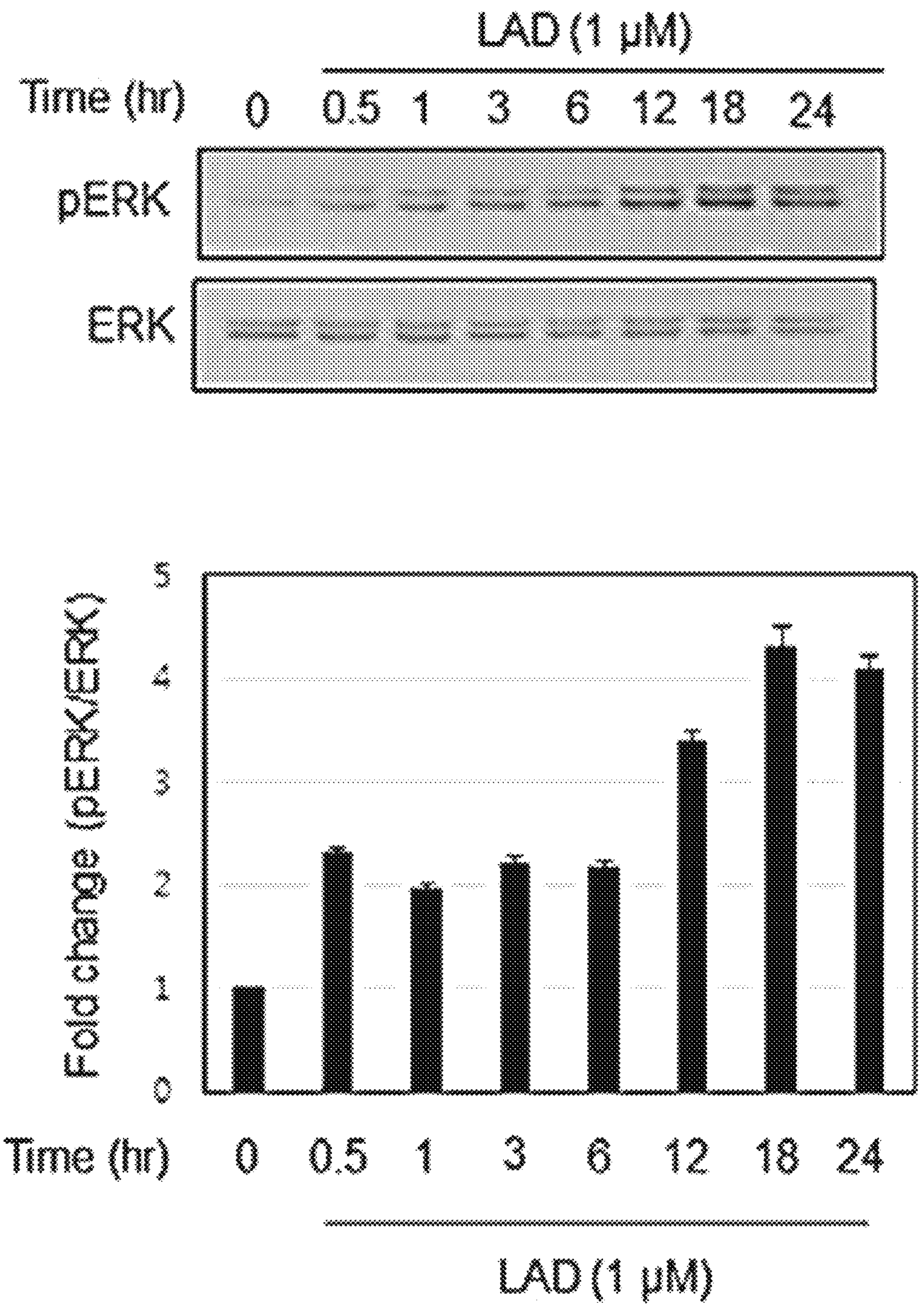
FIG. 6A shows the results of confirming a level of phosphorylated ERK (pERK) after mesenchymal stem cells are treated with the lappaconitine derivative (LAD) for 0 to 24 hours.

As a result, it can be seen that the level of phosphorylated ERK (pERK) significantly increased within 30 minutes after LAD treatment, and specifically that the level of phosphorylated ERK (pERK) increased even after 24 hours after LAD treatment (FIG. 6A).

Figure 6B:
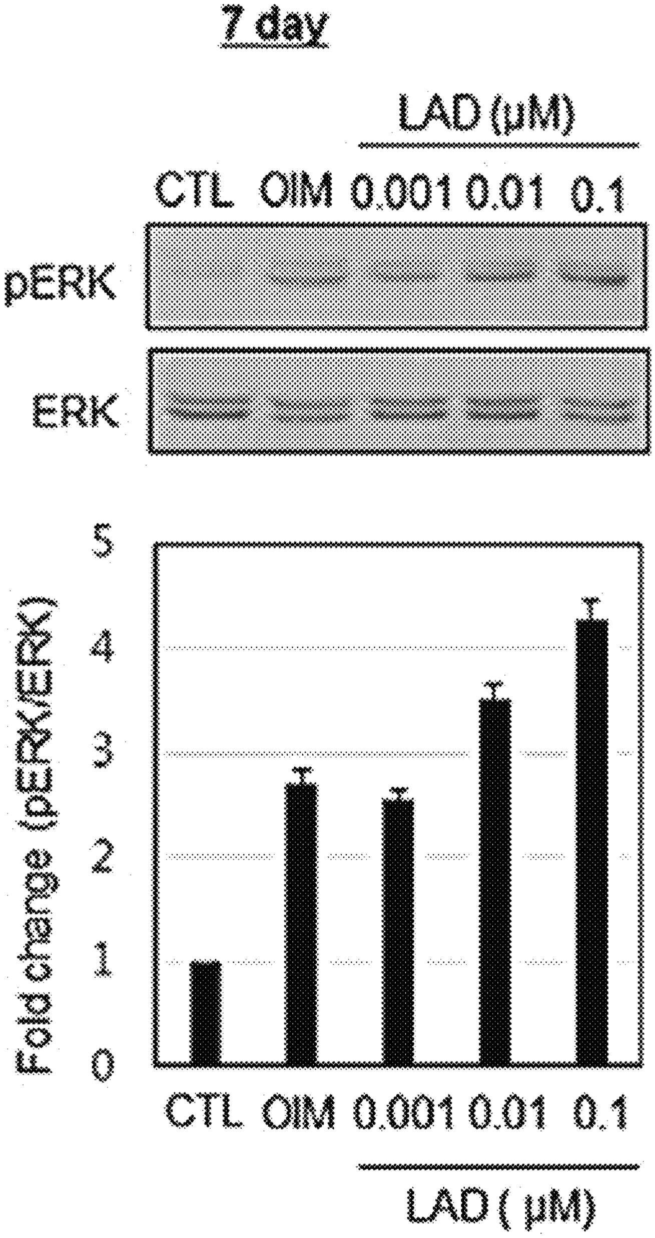
FIG. 6B shows the results of confirming a level of the phosphorylated ERK (pERK) after mesenchymal stem cells are treated with the lappaconitine derivative (LAD) for 7 days.
Figure 6C:
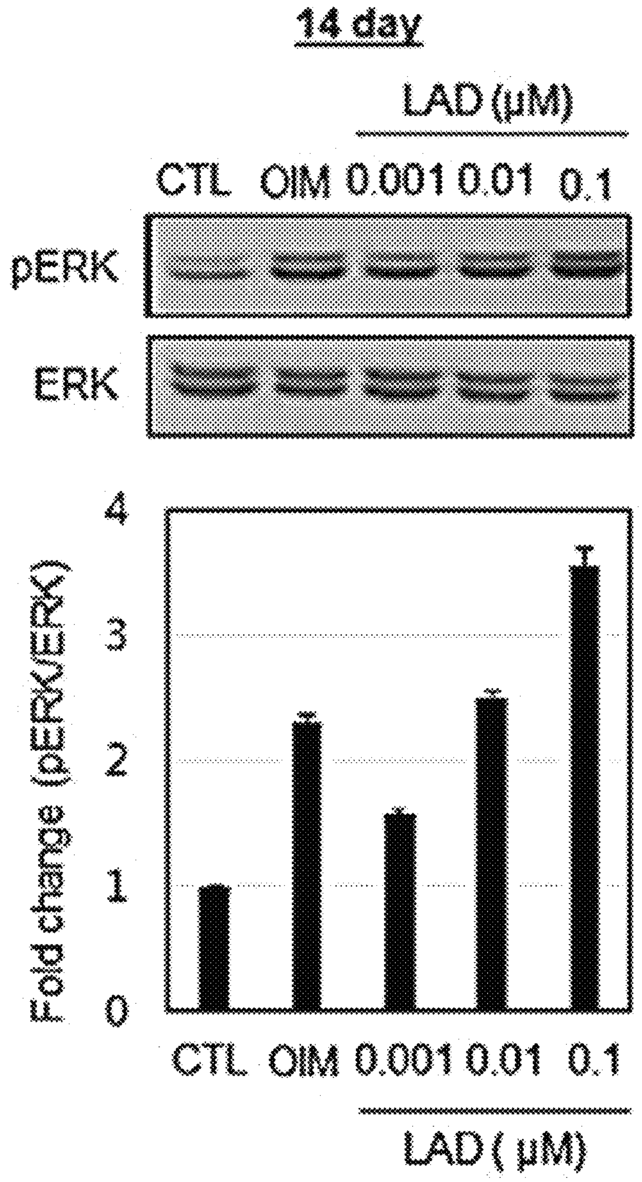
FIG. 6C shows the results of confirming a level of the phosphorylated ERK (pERK) after mesenchymal stem cells are treated with the lappaconitine derivative (LAD) for 14 days.

Also, to determine whether LAD induces the ERK phosphorylation for a long period, MSCs were treated with various concentrations (0.001, 0.01, and 0.1 μM) of LAD, and the level of phosphorylated ERK (pERK) was checked after 7 days and 14 days. As a result, it was confirmed that the level of phosphorylated ERK (pERK) significantly increased in all the experimental groups treated with LAD. In particular, it was confirmed that the level of phosphorylated ERK (pERK) increased to a level similar to that of the positive control (OIM) even at a low concentration. This tendency lasted until 14 days after LAD treatment, indicating that LAD increases ERK phosphorylation for a long period (FIGS. 6B and 6C).

These results indicate that the long-term activation of an ERK signaling mechanism by LAD is likely to be a key mechanism of the osteoblast differentiation capacity of LAD.

1-7. Confirmation of Effect of ERK Inhibitor on Increase in RUNX2 Expression by LAD ERK may induce the phosphorylation of RUNX2 to increase transcriptional activity and may be involved in stability to increase an amount of RUNX2 protein (Greenblatt et al., MB, Annu Rev Cell Dev Biol. 2013). Therefore, an increase in ERK phosphorylation by LAD may induce RUNX2 expression so that LAD can be involved in the differentiation of MSCs into osteoblasts. To verify this, an expression level of RUNX2 was determined after MSCs were treated with a combination of LAD (0.1 μM) and the ERK inhibitor PD98059 (50 μM).

Figure 7A:
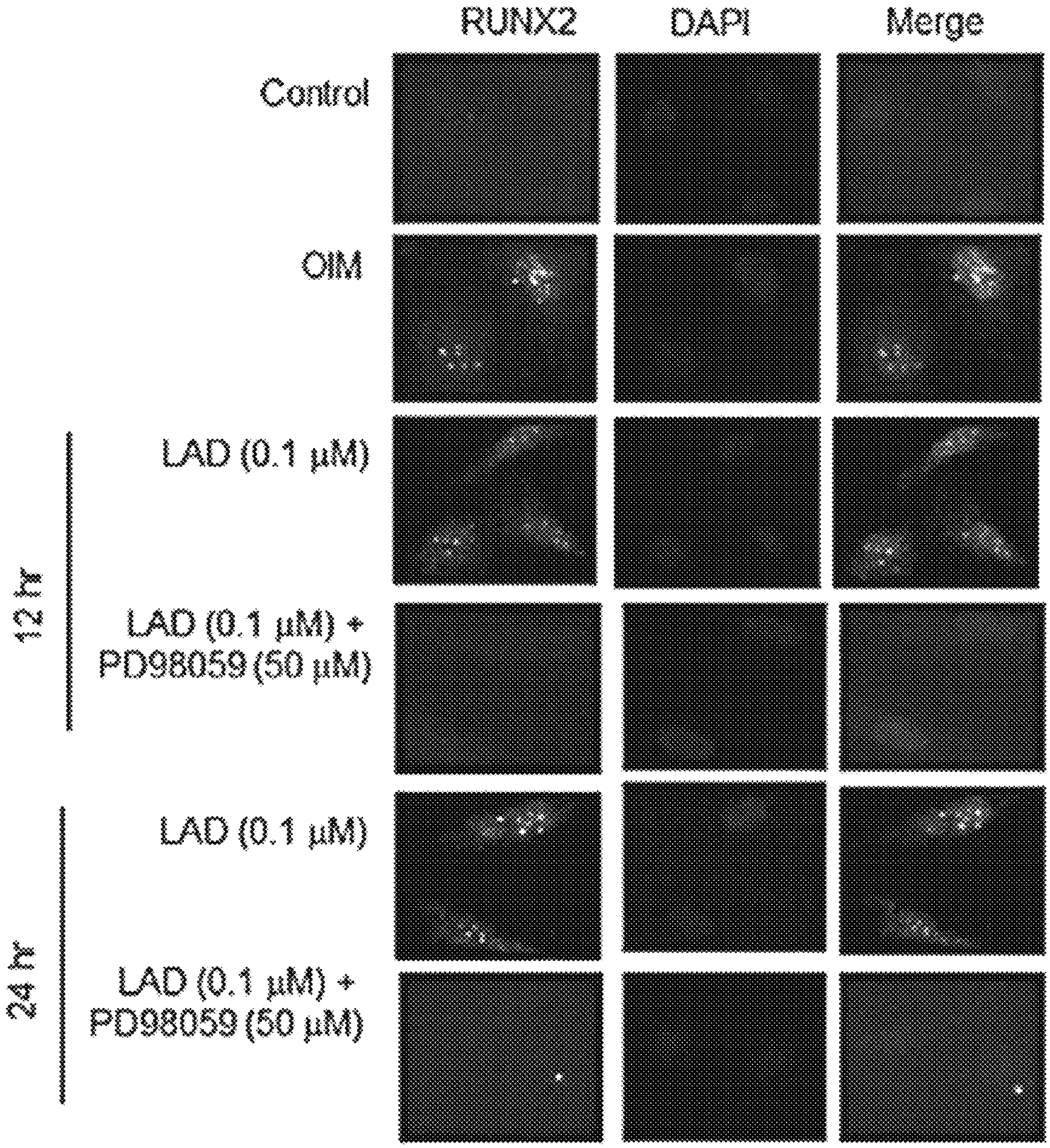
FIG. 7A shows the results of confirming a change in expression of RUNX2 using a fluorescence microscope after mesenchymal stem cells are treated with a combination of the lappaconitine derivative (LAD) and an ERK inhibitor (PD98059).
Figure 7B:
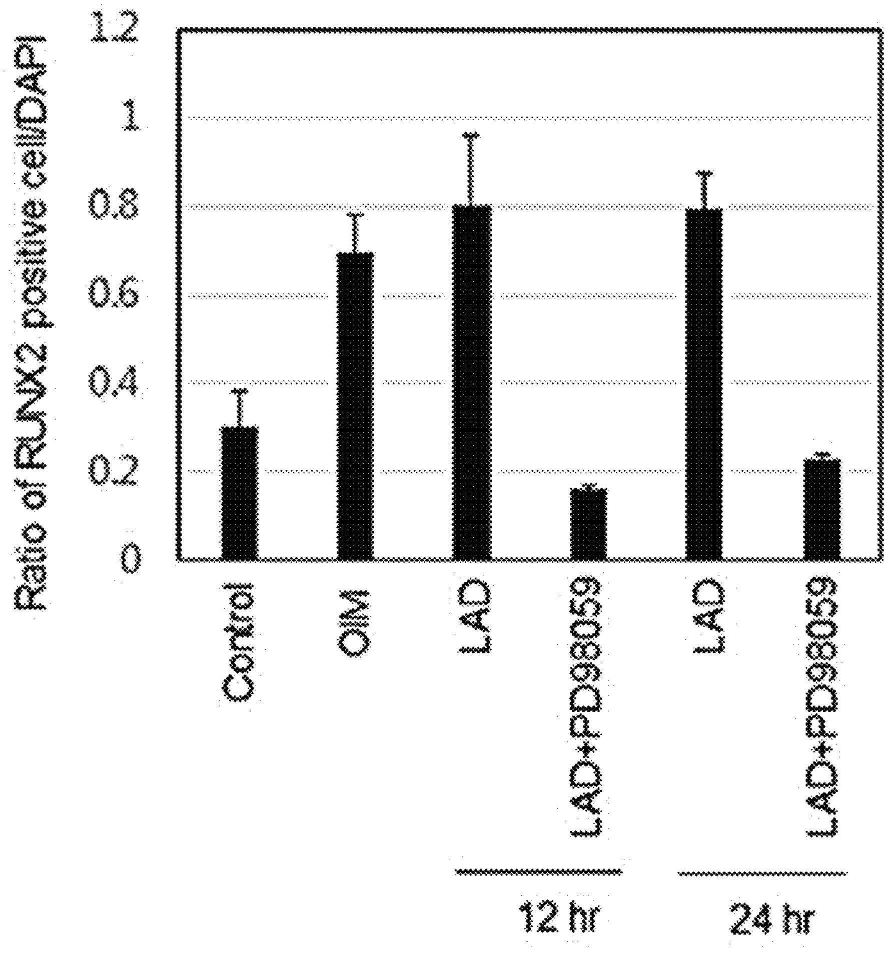
FIG. 7B is a graph showing the fluorescence levels of FIG. 7A.

As a result of confirmation, it can be seen that the expression of RUNX2 significantly increased within 12 hours after LAD treatment, but the expression of RUNX2 significantly decreased when MSCs were treated with a combination of LAD and the ERK inhibitor PD98059. The tendency was the same even 24 hours after LAD treatment (FIGS. 7A and 7B). The results show that the induction of ERK activation by LAD is a key mechanism of osteogenetic activity.

Experimental Example 2: (In Vivo) Confirmation of Efficacy of LAD

An ability of LAD to treat osteoporosis was confirmed in an animal model of ovariectomized (OVX) mice commonly used as an animal model of osteoporosis.

Figure 8A:
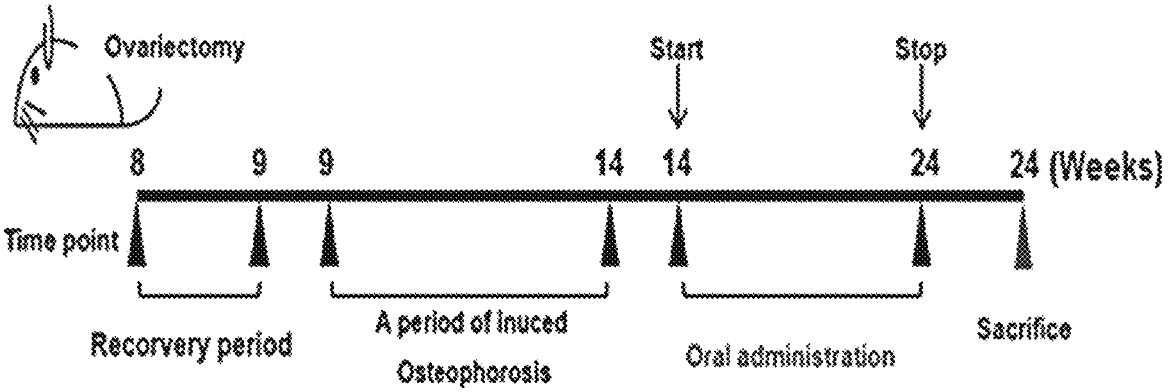
FIG. 8A shows the types of experimental groups and the schedule for administering the lappaconitine derivative (LAD) to an animal model of osteoporosis.

As the positive control, parathyroid hormone (PTH)-based Forteo (Eli Lilly) used as an osteoporosis therapeutic agent through an osteogenesis-promoting mechanism, and alendronate-based Fosamax (Merck) serving as a bone resorption inhibitor, were subcutaneously administered. As the negative control, water ($H_2O$) was orally administered, and LAD was orally administered at a concentration of 5 or 30 mg/kg (FIG. 8A). After the drug was administered daily for 10 weeks, the bone mineral density (BMD) was measured.

Figure 8B:
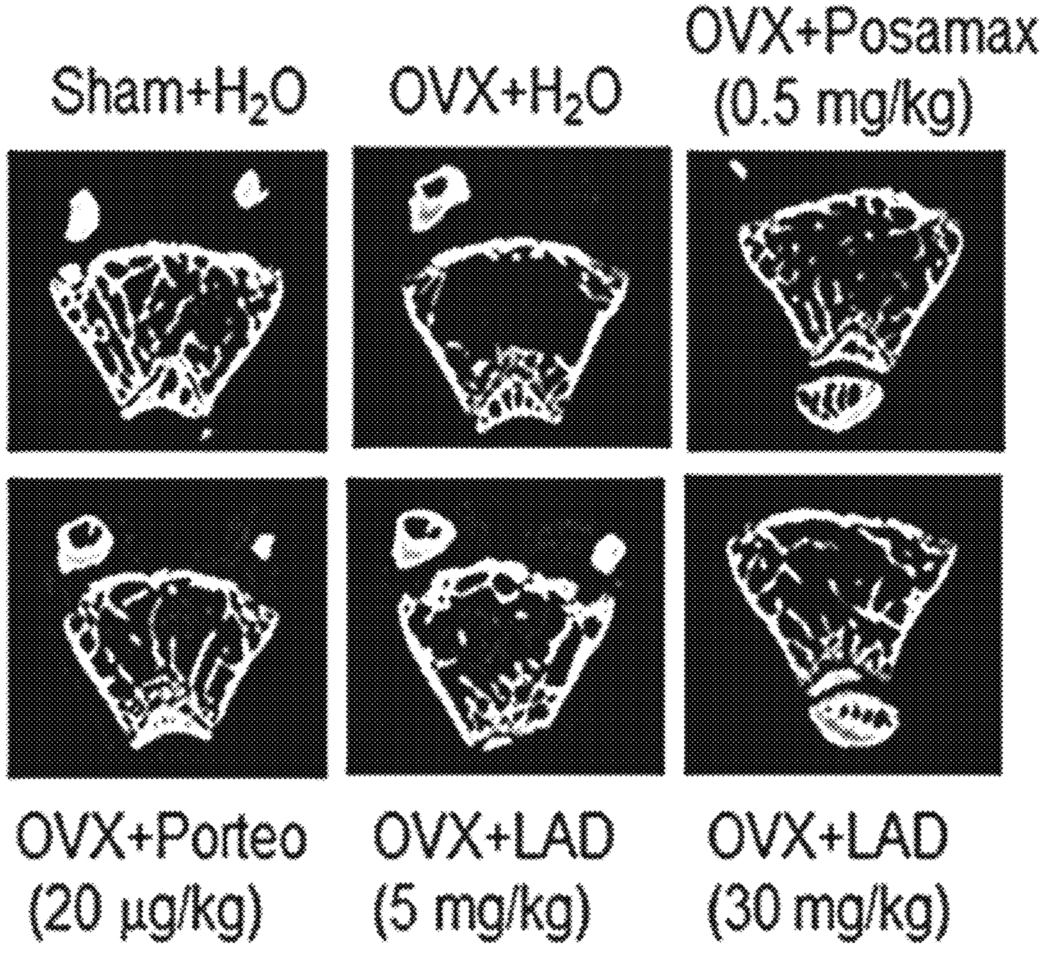
FIG. 8B shows the results of confirming the cross-sections of a femur after the lappaconitine derivative (LAD) is administered into an animal model of osteoporosis.
Figure 8C:
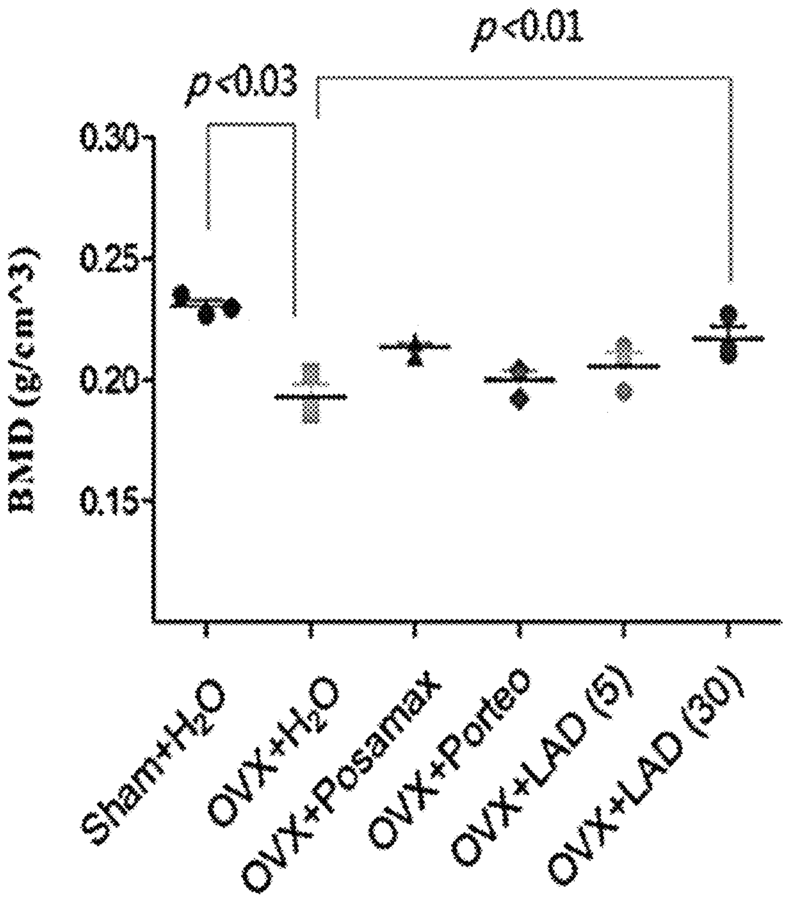
FIG. 8C shows the results of confirming the bone mineral density of a femur after the lappaconitine derivative (LAD) is administered into the animal model of osteoporosis.

As a result of measurement, it was confirmed that the bone mineral density significantly increased in the LAD-administered groups compared to the negative control, indicating that LAD had a therapeutic effect on osteoporosis. In this case, the effect of LAD was similar to that of Fosamax, and significantly superior to that of Forteo (FIGS. 8B and 8C).

Figure 9A:
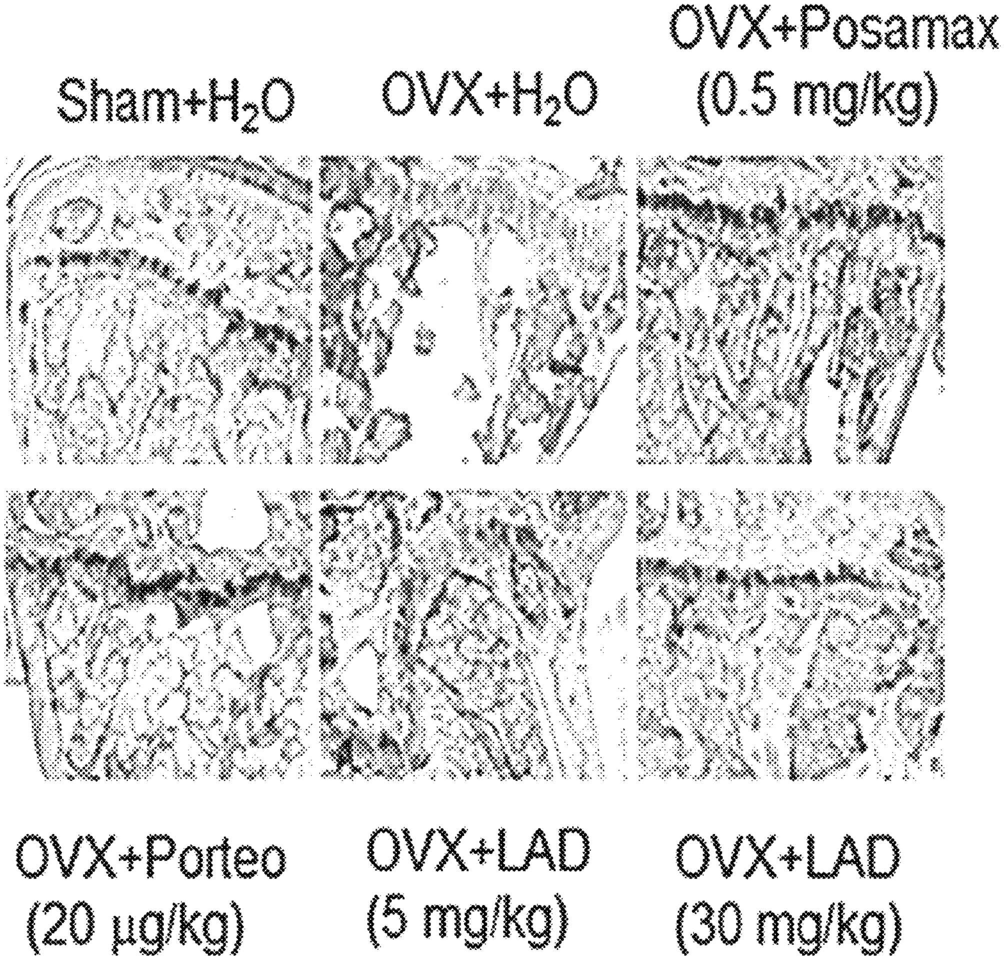
FIG. 9A shows the results of confirming a level of osteogenesis after the lappaconitine derivative (LAD) is administered into the animal model of osteoporosis.
Figure 9B:
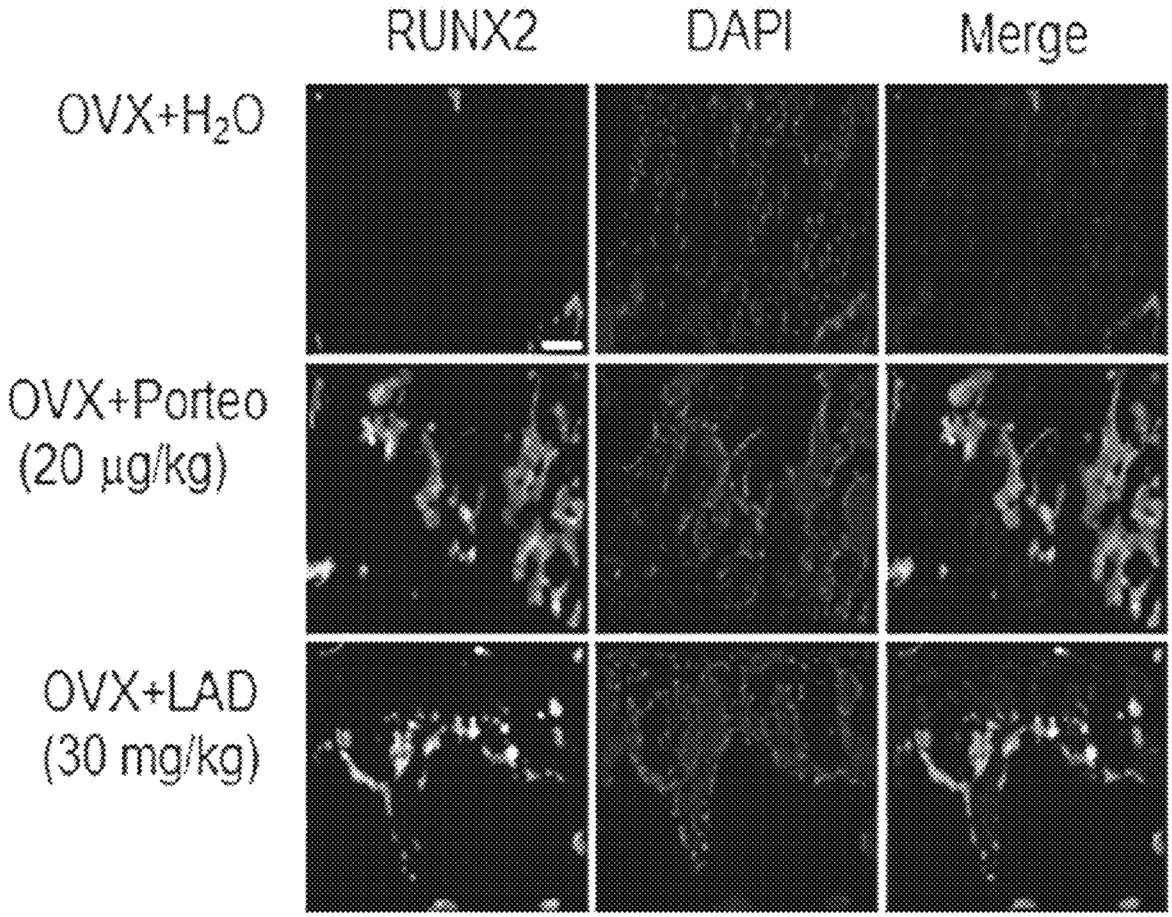
FIG. 9B shows the results of confirming an expression level of RUNX2 after the lappaconitine derivative (LAD) is administered into the animal model of osteoporosis.

Based on the tissue staining results, it can also be seen that LAD induced osteogenesis in the femurs of ovariectomized mice (FIG. 9A), and the expression of RUNX2, which is a transcription factor involved in osteogenesis, also significantly increased (FIG. 9B). The experimental results are summarized in Table 1 below. In Table 1, BMD represents bone mineral density, TV represents total volume, BV represents bone volume, Tb.Th represents trabecular thickness, and Tb.N represents trabecular number.

TABLE 1

| Group | BMD (g/cm^3) | TV (mm^3) | BV (mm^3) | BV/TV (%) | Tb. Th (1/mm) | Tb. N (mm) |
|---|---|---|---|---|---|---|
| Sham + $H_2O$ | 0.235060 | 15.062852 | 1.225416 | 8.173108 | 0.078936 | 1.034056 |
| OVX + $H_2O$ | 0.194646 | 14.942314 | 0.734676 | 4.959768 | 0.073672 | 0.670696 |
| OVX + Fosamax | 0.214462 | 15.509586 | 1.017400 | 6.521050 | 0.069936 | 0.928632 |
| OVX + Forteo | 0.201314 | 15.431426 | 0.879062 | 5.734686 | 0.071124 | 0.801822 |
| OVX + LAD (5) | 0.206636 | 15.596182 | 1.009140 | 6.421504 | 0.204976 | 0.877496 |
| OVX + LAD (30) | 0.216824 | 16.580030 | 1.169798 | 7.036494 | 0.073904 | 0.948470 |

Based on the results, it was confirmed that the LAD compound of the present invention induced calcium and mineral production in MSCs, increased the expression of RUNX2, BMP-2, and osteocalcin, and induced ERK activation to induce osteoblast differentiation. Also, the LAD compound may be effectively used to treat bone-related diseases such as osteoporosis because the LAD compound increases bone mineral density and induces osteogenesis when administered to an animal model of osteoporosis.

FORMULATION EXAMPLES

Meanwhile, the novel compound LAD according to the present invention may be formulated into various forms according to a purpose. Hereinafter, methods of formulating a composition including the novel compound LAD of the present invention as an active ingredient are described for illustrative purposes, but the present invention is not limited thereto.

1. Tablet (Direct Pressing)

5.0 mg of the active ingredient was sieved, mixed with 14.1 mg of lactose, 0.8 mg of crospovidone USNF, and 0.1 mg of magnesium stearate, and then pressed to prepare tablets.

2. Tablet (Wet Assembly)

5.0 mg of the active ingredient was sieved, and then mixed with 16.0 mg of lactose and 4.0 mg of starch. 0.3 mg of polysorbate 80 was dissolved in pure water, and a suitable amount of this solution was then added to the mixture for granulation. After drying, fine granules were sieved, and then mixed with 2.7 mg of colloidal silicon dioxide and 2.0 mg of magnesium stearate. The fine granules were pressed to prepare tablets.

3. Powder and Capsule 5.0 mg of the active ingredient was sieved, and then mixed with 14.8 mg of lactose, 10.0 mg of polyvinyl pyrrolidone, and 0.2 mg of magnesium stearate. The mixture was filled into hard No. 5 gelatin capsules using a suitable device.

4. Injection 100 mg of the active ingredient, 180 mg of mannitol, and 26 mg of $Na_2HPO_4/H_2O$ were dissolved in 2,974 mg of distilled water to prepare an injection.

The invention claimed is:

1. A compound represented by the following Formula 1, and a stereoisomer, a hydrate, or a pharmaceutically acceptable salt thereof:

[Formula 1]

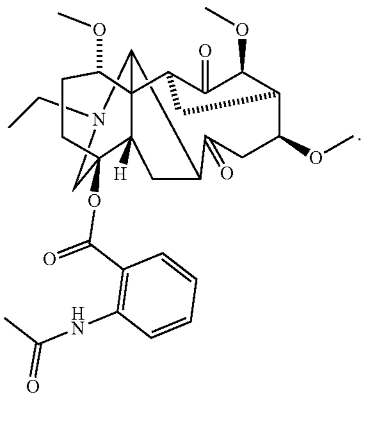

2. A pharmaceutical composition for treating a bone-related disease, comprising a compound represented by the following Formula 1, and a stereoisomer, a hydrate, or a pharmaceutically acceptable salt thereof as an active ingredient, wherein the bone-related disease is selected from the group consisting of osteoporosis, bone fractures, osteomalacia, osteopenia, bone atrophy, osteoarthritis, bone defects, osteolysis, and osteonecrosis:

[Formula 1]

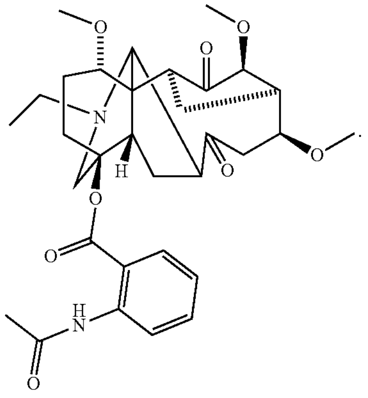

3. The pharmaceutical composition of claim 2, wherein the compound represented by Formula 1 promotes the differentiation of stem cells into osteoblasts.

4. The pharmaceutical composition of claim 2, wherein the compound represented by Formula 1 increases the expression of an osteogenic marker selected from the group consisting of runt-related transcription factor 2 (RUNX2), bone morphogenetic protein 2 (BMP2), and osteocalcin.

5. A food composition for ameliorating a bone-related disease, comprising the compound of claim 1 as an active ingredient, wherein the bone-related disease is selected from the group consisting of osteoporosis, bone fractures, osteomalacia, osteopenia, bone atrophy, osteoarthritis, bone defects, osteolysis, and osteonecrosis.

6. The food composition of claim 5, wherein the compound represented by Formula 1 promotes the differentiation of stem cells into osteoblasts.

7. A method of synthesizing a compound represented by the following Formula 1, comprising:

allowing lappaconitine to react with an oxidizing agent:

[Formula 1]

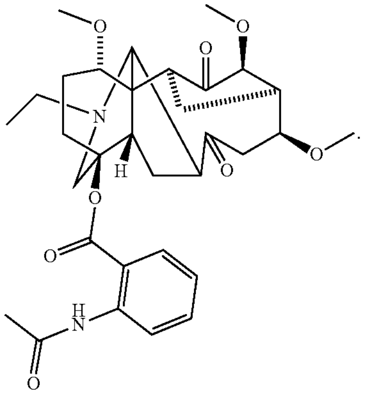

8. The method of claim 7, wherein the oxidizing agent is selected from the group consisting of phenyliodine diacetate ($PhI(OAc)_2$), lead (II) acetate ($Pb(CH_3CO_2)_2$), lead (IV) acetate ($Pb(CH_3CO_2)_4$), ozone, and $HIO_4$.

9. A method of treating a bone-related disease, comprising:

administering the pharmaceutical composition of claim 2 to a subject in need thereof, wherein the bone-related disease is selected from the group consisting of osteoporosis, bone fractures, osteomalacia, osteopenia, bone atrophy, osteoarthritis, bone defects, osteolysis, and osteonecrosis.

* * * * *